United States Patent
Madhavi et al.

(10) Patent No.: US 6,380,442 B1
(45) Date of Patent: Apr. 30, 2002

(54) PROCESS FOR THE ISOLATION OF MIXED CAROTENOIDS FROM PLANTS

(75) Inventors: Doddabele L. Madhavi, Worcester; Daniel I. Kagan, Belmont, both of MA (US)

(73) Assignee: BioActives, LLC, Belmont, MA (US)

( * ) Notice: Subject to any disclaimer, the term of this patent is extended or adjusted under 35 U.S.C. 154(b) by 0 days.

(21) Appl. No.: 09/974,141

(22) Filed: Oct. 10, 2001

(51) Int. Cl.[7] ............................................. C07C 35/21
(52) U.S. Cl. ...................................................... 568/816
(58) Field of Search ......................................... 568/816

(56) References Cited

U.S. PATENT DOCUMENTS 3,523,138 A * 8/1970 Grant
5,382,714 A * 1/1995 Khachik
5,648,564 A * 7/1997 Ausich
6,262,284 B1 * 7/2001 Khachik

* cited by examiner

Primary Examiner—Michael L. Shippen
(74) Attorney, Agent, or Firm—Mueller and Smith, LPA

(57) ABSTRACT

A practical and effective process for isolating and purifying mixed carotenoids containing higher concentrations of specific compounds, such as all-trans lutein, without the use of harmful organic solvents, is disclosed. The process employs hydrolysis of carotenoid esters in a mixture of isopropanol, water, and alkali to separate the carotenoids from other impurities. The carotenoids are purified further using aqueous precipitation, followed by centrifugation and drying under vacuum. The product is a fine crystalline powder with very low residual solvents (hexane 0.22 ppm; isopropanol 0.53 ppm) suitable for human consumption, either in nutritional supplements or as a food additive.

12 Claims, No Drawings

PROCESS FOR THE ISOLATION OF MIXED CAROTENOIDS FROM PLANTS

CROSS-REFERENCE TO RELATED APPLICATIONS

None

STATEMENT REGARDING FEDERALLY SPONSORED RESEARCH

Not applicable.

BACKGROUND OF THE INVENTION

The present invention relates to carotenoids that have beneficial effects in humans and more particularly to lutein and its production.

Lutein, (3R,3'R,6'R)-β,ε-carotene-3,3'-diol, has three asymmetric centers, C-3, C-3', and C-6'. The absolute configuration of lutein in foods and human serum/plasma is known to be 3R,3'R,6'R. In small trace amounts, another configurational isomer of lutein (3R,3'S,6'R) also has been shown to be present in human sera. Of special importance for present purposes is the all-trans isomer or E-isomer of lutein.

In recent years, human and animal studies have established the various beneficial effects of carotenoids, especially lutein and zeaxanthin, in preventing age related macular degeneration and various forms of cancer, due to their antioxidant activity. Fruits and vegetables are the richest sources of a variety of natural carotenoids, of which some are present in only trace amounts. Most of the earlier studies and isolation processes related to carotenoids were targeted towards individual compounds, such as, β-carotene, lycopene, and lutein. However, recent studies indicate that a mixture of carotenoids may have additional beneficial effects over pure compounds due to synergistic effects. Hence, development of a commercial process for the production of dietary carotenoid mixtures enriched in one or more carotenoids, such as all-trans lutein, may be of importance. These mixtures can be used in nutritional supplements or as food additives.

Although present in green vegetables, yellow/orange fruits and vegetables, marigold flower petals are one of the richest sources of lutein, along with other carotenoids, which occur acylated with fatty acids. The petals are extracted with a lipophilic solvent and the esters are hydrolyzed by saponification to obtain lutein, along with other carotenoids, in free form. Several patents and publications propose the isolation of lutein from marigold petals on a commercial scale. The publications in general focus on isolation of lutein in a pure form and involve multiple process steps.

U.S. Pat. No. 5,382,714 reports that saponified marigold oleoresin from Kemin Industries (Des Moines, Iowa) containing free lutein is the preferred starting material for the isolation of pure lutein. The purification steps involve multiple solvents, cold temperatures, and are very time consuming in commercial production.

U.S. Pat. No. 5,648,567 teaches a process for the isolation of lutein from marigold oleoresin at 74% purity. This process employs propylene glycol and an aqueous alkali to saponify a hexane extract of dried marigold petals containing lutein esters at 70° C. in 10 hours. The process has several disadvantages. For example, the hydrolysis of lutein and zeaxanthin esters in the marigold oleoresin is conducted in an aqueous solution in the presence of propylene glycol, in which the fatty acid esters of lutein and zeaxanthin have very low solubility. As a result, this process requires high temperatures of up to 70° C. and 10 hours to complete the saponification on a commercial scale. This can result in the degradation and unwanted isomerization of lutein and zeaxanthin. Additionally, due to the high viscosity of propylene glycol, the saponified product is continuously subjected to high temperatures ranging from 70° to 85° C. during handling and several purification steps. This unnecessary exposure to heat in the presence of air can result in oxidative degradation of lutein and zeaxanthin with the consequent formation of a number of degradation side products.

U.S. Pat. No. 6,262,284) describes the simultaneous extraction and saponification of carotenoids from marigold dry flower petals. Again, the process has several drawbacks. Marigold petals contain a maximum of 1–2% total carotenoids. The dry petals are extracted using tetrahydrofuran at a 1:10 dry matter to solvent ratio. The extract is used for saponification without further concentration, which results in the use of large volumes of solvent during commercial production. The solvent also is unstable and produces peroxides, which may degrade the carotenoids. The low levels of carotenoids in the meal combined with the high solvent to meal ratio and the final recrystallization step make commercial viability of the process doubtful.

BRIEF SUMMARY OF THE INVENTION

The present invention is a convenient and effective process to isolate carotenoids, especially lutein, from marigold oleoresin (as the preferred source) with minimal use of organic solvents. The process involves hydrolysis of the carotenoid esters in marigold oleoresin using isopropanol, water, and alkali, for a minimum of 60 to 90 minutes at a temperature of about 60° to 65° C. The hydrolyzed carotenoids are precipitated from the saponified mixture using water. The precipitate is recovered by centrifugation, followed by purification of the precipitate with repeated water washings, and a drying step to obtain a fine crystalline material.

The process can be used to recover the carotenoids from oleoresins or extracts containing low levels of carotenoids, a mixture of oleoresins with different carotenoid profiles, and oleoresins obtained by supercritical extraction. In the case of plant extracts containing the carotenoids in a free form, such as, for example, spinach, the saponification step separates the carotenoids from chlorophyll and other contaminants.

Advantages of the present invention include, inter alia, hydrolysis of the esters can be efficiently completed at a lower temperature and in a shorter duration of time, because the oleoresin is completely soluble in isopropanol at a temperature of about 60° to 65° C. Another advantage is that the remaining process steps are carried out at room temperature, thus reducing the risk of oxidative degradation of carotenoids. As further advantage, the process recovers even the trace amount of other carotenoids present in the oleoresin in addition to the recovery of major carotenoids. Yet further advantages are that, the process is less time consuming, economical, and commercially feasible compared to prior processes, because the invention does not involve use of multiple solvent extractions or recrystallization steps. These and other advantages will become readily apparent to those skilled in the art based on the disclosure set forth herein.

DETAILED DESCRIPTION OF THE INVENTION

The invention is the isolation of carotenoid mixtures containing high levels of desired specific compounds from plant extracts known to synthesize the desired compounds at high concentrations. Specifically, commercially available food grade marigold oleoresin produced by hexane extraction can be used as the starting material for the isolation of an all-trans lutein enriched product. Marigold flower (Tagetes sp., such as *Tagetes erecta*) is reputed to be the best possible commercial source for all-trans lutein as it contains lutein mono and diesters as the major carotenoid constituents. Marigold oleoresin obtained from the dry flower petals contains around 5% to 20% lutein esters, based on the cultivar and the extraction process. In addition to lutein, marigold oleoresin also contains all-trans zeaxanthin, $\alpha$- and $\beta$-cryptoxanthin, $\beta$-carotene, and traces of other carotenoids.

In the present invention, the oleoresin is dissolved in food grade isopropanol to form a free flowing solution at a temperature within the range of from about 60° to 65° C. In a typical process, one weight part of the oleoresin is dissolved in excess (e.g., 2–3 volume parts) of the solvent. The impurities present in the oleoresin, such as, waxes, resins, and non-carotenoid pigments, also are soluble in isopropanol.

An aqueous 50% potassium hydroxide solution, for example, is added to the solution under constant agitation. The amount of the alkali required is approximately 1.5 to 2 times the concentration of the total carotenoid esters in the oleoresin. The mixture is maintained at the same temperature under agitation for a time period ranging from about 60 to 90 minutes and until the saponification (for example, as determined by thin layer chromatography) is complete. Additional alkali metal (Group 1a metals, for example, Li, Na, K) and alkaline earth metal (Group 2a metal, for example, Mg, Ca, Ba) bases can be used in addition to the preferred KOH. Accordingly, alkali metal and alkaline earth metal hydroxides can be used as is necessary, desirable, or convenient.

The reaction mixture is allowed to cool to room temperature, resulting in the formation of a semi-solid mass. The mixture, then, is dispersed in a sufficient quantity of water to reduce the solvent concentration to about 40%–50% (volume/volume) with gentle mixing. The solution is allowed to stand at room temperature for about 1–4 hours until the lutein and other carotenoids separate as a fine crystalline precipitate.

A lutein enriched mixed carotenoid product then is recovered. Recovery can include, for example, diluting the mixture further with water to reduce the solvent (isopropanol) level to about 20%–25% just prior to centrifugation. Any state of the art (preferably) continuous flow centrifugation equipment can be used to collect the fine precipitate. The impurities, such as salts of fatty acids, are removed in the supernatant, as these impurities are soluble in the isopropanol-water mixture.

Additional recovery efforts may include, for example, that the precipitate, then, can be washed with additional water or isopropanol-water mixture until the supernatant becomes almost colorless. Usually 2–3 washes are sufficient to remove most of the contaminants. The washed precipitate is dried by a suitable method, such as, for example, vacuum drying at 40° C. or freeze drying, preferably until the moisture level is reduced to less than about 5%.

The resulting product contains between about 53% and 95% (weight/weight) total carotenoids and between about 50% and 88% all-trans lutein (based on spectrophotometry and reverse phase HPLC). The concentration of lutein and the total carotenoids varies based on the organic solvent percentage and the time of precipitation. The solvent percentage in the diluted saponified material has been found to be important in determining the purity and overall yield of the final product. The final product generally contains less than about 0.5 ppm hexane and less than about 1 ppm isopropanol.

While the invention has been described with reference to a preferred embodiment, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In this application all units are in the metric system and all amounts and percentages are by weight, unless otherwise expressly indicated. Also, all citations referred herein are expressly incorporated herein by reference.

The following examples are offered to illustrate but not limit the present invention.

EXAMPLES

Example 1

One kilogram of marigold oleoresin containing 11% (weight/weight) total carotenoids (approximately 8% lutein esters) was mixed with 3 liters of isopropanol with stirring and heated to a temperature of 60° C. until a free flowing solution was obtained. An aqueous 50% potassium hydroxide solution, equivalent to 220 g of the alkali, was added slowly and the solution was maintained at 60°–65° C. with stirring for a period of 90 min. The saponified mixture was allowed to cool to room temperature and then diluted with deionized water to reduce the solvent concentration to approximately 50% (volume/volume) with gentle mixing. The mixture was allowed to stand for approximately 60 min followed by addition of 4 times (v/v) deionized water just before centrifugation. The fine crystalline precipitate was collected using a Sharples tubular bowl centrifuge. The precipitate was washed twice with additional water and was dried under vacuum at 40° C. to less than 5% moisture content.

The yield of the final product was 7%, which contained 95% total carotenoids (as determined by spectrophotometry) of which 90% was all-trans lutein, 4% was all-trans zeaxanthin (as determined by HPLC), and the rest contained traces of other carotenoids. The recovery of lutein was 75% of the total lutein present in the oleoresin. The final product contained 0.22 ppm hexane and 0.53 ppm of isopropanol, as determined by headspace gas chromatographic analysis.

Example 2

This study was performed using an oleoresin containing 5.8% (weight/weight) of lutein esters using the same method reported in Example 1, except that the solvent percentage was maintained at 50% during washing of the saponified mixture. The yield of the final product was at 6.6% containing 78% total carotenoids, of which 89% was all-trans lutein. A reduction in the solvent percentage to 20% or below resulted in a product containing approximately 50% lutein. Again, the efficacy of the present invention is demonstrated.

What is claimed is:

1. A method for producing a lutein enriched mixed carotenoid product from a lutein ester source, comprising the steps of:
   (a) dissolving the lutein ester source in isopropanol solvent at a temperature ranging from about 60° to 65° C. to form a free-flowing solution of carotenoids;
   (b) hydrolyzing said dissolved lutein ester source with excess aqueous saponification agent;
   (c) cooling said hydrolyzed solution to about ambient temperature;
   (d) adding aqueous solvent to said cooled solution to precipitate a carotenoid product;
   (e) recovering said precipitated carotenoid product.

2. The method of claim 1, wherein said lutein ester source comprises marigold flower extract.

3. The method of claim 1, wherein said saponification agent comprises an alkali metal or alkaline earth metal base.

4. The method of claim 3, wherein said saponification agent comprises potassium hydroxide.

5. The method of claim 1, wherein the weight to volume ratio of lutein ester source to isopropanol solvent in step (a) ranges from about 2 to 3.

6. The method of claim 1, wherein said recovery comprises the addition of additional water to reduce the isopropanol content to between about 20% and 25%, followed by centrifugation.

7. The method of claim 6, wherein said recovered carotenoid product is washed with additional aqueous solvent.

8. The method of claim 7, wherein said washed recovered carotenoid product is dried to a moisture content of less than about 5 weight-%.

9. The method of claim 8, wherein said drying is by one or more of vacuum drying or freeze drying.

10. The method of claim 1, wherein said recovered carotenoid product contains between about 53% and 95% by weight of the total carotenoids in the lutein ester source.

11. The method of claim 10, wherein said recovered carotenoid product contains between about 50% and 88% all-trans lutein.

12. The method of claim 11, wherein the concentration of said lutein in said precipitated carotenoid product is controlled based on the concentration of isopropanol solvent and time of precipitation of said carotenoid product in step (d).

* * * * *